United States Patent
Kohler et al.

(10) Patent No.: US 6,746,647 B2
(45) Date of Patent: Jun. 8, 2004

(54) METHOD FOR RAPIDLY STERILIZING A LOAD

(76) Inventors: James P. Kohler, 25221 Champlain Rd., Laguna Hills, CA (US) 92653; Nancy S. Chu, 29405 Ana Maria, Laguna Niguel, CA (US) 92677

( * ) Notice: Subject to any disclaimer, the term of this patent is extended or adjusted under 35 U.S.C. 154(b) by 0 days.

(21) Appl. No.: 10/379,518

(22) Filed: Mar. 4, 2003

(65) Prior Publication Data

US 2003/0156977 A1 Aug. 21, 2003

Related U.S. Application Data

(63) Continuation of application No. 09/604,650, filed on Jun. 27, 2000, now Pat. No. 6,528,016.

(51) Int. Cl.[7] .................................................. A61L 2/00
(52) U.S. Cl. ................................. 422/28; 422/1; 422/3; 422/22; 422/23; 422/105; 422/107; 422/119
(58) Field of Search ............................ 422/1, 3, 28, 22, 422/23, 105, 107, 119

(56) References Cited

U.S. PATENT DOCUMENTS

| 4,643,876 A | 2/1987 | Jacobs et al. |
| 4,687,635 A | 8/1987 | Kaehler et al. |
| 4,756,882 A | 7/1988 | Jacobs et al. |
| 4,843,867 A | 7/1989 | Cummings |
| 4,956,145 A | 9/1990 | Cummings et al. |
| 5,565,634 A | 10/1996 | Graessle et al. |
| 5,608,156 A | 3/1997 | Ando et al. |
| 5,656,238 A | 8/1997 | Spencer et al. |
| 6,060,019 A | 5/2000 | Spencer et al. |
| 6,156,267 A | 12/2000 | Pai et al. |
| 6,528,016 B1 * | 3/2003 | Kohler et al. ................ 422/28 |

FOREIGN PATENT DOCUMENTS

| EP | 0 016 888 A | 10/1980 |
| EP | 1 016 421 A | 7/2000 |
| WO | WO 98 00176 A | 1/1998 |

* cited by examiner

Primary Examiner—Krisanne Thornton

(57) ABSTRACT

A method is provided for rapidly determining whether a load of equipment to be sterilized in a sterilization chamber absorbs, adsorbs, condenses, or decomposes significant amounts of germicide vapor or gas, such as hydrogen peroxide. The initial slope of the curve of a plot of $\ln(c/c_0)$ versus time is determined, where c is the concentration of hydrogen peroxide and $c_0$ is the maximum concentration of hydrogen peroxide. The initial slope is determined in the first 100 seconds after the maximum in the concentration of hydrogen peroxide. If the initial slope is approximately $0.016\ \text{sec}^{-1}$ or less, the load is acceptable. If the initial slope is significantly steeper than $0.016\ \text{sec}^{-1}$, the load absorbs, adsorbs, condenses, or decomposes significant amounts of hydrogen peroxide. If the slope of the curve is steep, the system can abort the sterilization run before significant amounts of hydrogen peroxide have been absorbed, adsorbed, or condensed.

23 Claims, 9 Drawing Sheets

METHOD FOR RAPIDLY STERILIZING A LOAD

RELATED APPLICATIONS

This application is a continuation of U.S. application Ser. No. 09/604,650, filed Jun. 27, 2000, now U.S. Pat. No. 6,528,016, which is incorporated herein by reference in its entirety.

BACKGROUND OF THE INVENTION

1. Field of the Invention

This invention relates to a method of rapidly determining the acceptability of a load of devices to be sterilized by chemical sterilization with a germicide gas or vapor, for example, with hydrogen peroxide.

2. Description of the Related Art

The need to sterilize articles such as medical devices is well known. There are many methods of sterilization, including heat and chemical methods. Heat sterilization is normally done with steam. The heat and/or moisture from the steam can damage sensitive medical devices. As a result, chemical sterilization is commonly used to minimize damage to medical devices during sterilization.

Chemical sterilization uses a sterilizing fluid such as hydrogen peroxide, ethylene oxide, chlorine dioxide, formaldehyde, or peracetic acid in a sealed chamber to sterilize medical instruments. One commercial form of chemical sterilization is the STERRAD® Sterilization System, available through Advanced Sterilization Products of Irvine, Calif., a division of Ethicon, Inc. The STERRAD Process utilizes hydrogen peroxide and low temperature gas plasma to sterilize medical devices.

The STERRAD Sterilization Process is performed in the following manner. The items to be sterilized are placed in a sterilization chamber, the chamber is closed, and a vacuum is drawn. An aqueous solution of hydrogen peroxide is injected and vaporized into the chamber. A low-temperature gas plasma is initiated by applying radio frequency energy to create an electric field. The hydrogen peroxide vapor dissociates in the plasma into reactive species that react with and kill microorganisms. After the activated components react with the organisms or with each other, they lose their high energy and recombine to form oxygen, water, and other nontoxic byproducts. At the completion of the process, the RF energy is turned off, the vacuum is released, and the chamber is returned to atmospheric pressure by venting.

In order for the sterilization process to be effective, sufficient hydrogen peroxide must be introduced into the chamber. If the equipment in the chamber reacts with, absorbs, adsorbs, or condenses the hydrogen peroxide, there may not be sufficient hydrogen peroxide remaining in the chamber for the sterilization process to be effective. The concentration of hydrogen peroxide vapor in the chamber is therefore monitored to assure that sufficient hydrogen peroxide is present. If too much hydrogen peroxide is removed from the chamber through absorption, adsorption, condensation, or reaction with the equipment in the chamber, the cycle is canceled, the remaining hydrogen peroxide in the chamber is removed by evacuating the chamber and/or introducing plasma to decompose the hydrogen peroxide, and a new cycle is started.

Cummings et al. (U.S. Pat. No. 4,956,145) describe a method in which the hydrogen peroxide concentration is monitored, and additional hydrogen peroxide is added to maintain the concentration of hydrogen peroxide at a level which is effective for sterilization but is less than the saturation limit. Cummings et al. did not describe any method for determining whether the equipment in the sterilization chamber significantly absorbs, adsorbs, condenses, or decomposes large amounts of hydrogen peroxide, however. If hydrogen peroxide is absorbed, adsorbed, or condensed onto the equipment, it may take a great deal of time to remove the hydrogen peroxide so that the equipment may be safely removed from the chamber.

There is a need for a method for rapidly determining whether the load of equipment in the chamber is suitable or not so that the sterilization cycle can be canceled before significant amounts of hydrogen peroxide have been absorbed, adsorbed, or condensed onto the equipment. If the unsuitability of the load could be determined rapidly, the cycle can be aborted and the hydrogen peroxide removed from the chamber before significant amounts of hydrogen peroxide have been absorbed, adsorbed, or condensed by the equipment in the chamber. In this manner, the length of time required to abort the cycle and start a new cycle can be minimized.

SUMMARY OF THE INVENTION

One aspect of the invention involves a method for sterilizing a load with a germicide vapor or gas including placing the load into a sterilization chamber, evacuating the sterilization chamber, and contacting the load in the sterilization chamber with the germicide vapor or gas. The method also includes monitoring the concentration of the germicide vapor or gas in the sterilization chamber as a function of time, determining the rate of change of the concentration of the germicide vapor or gas in the sterilization chamber, and determining the suitability of the load from the rate of change. The load is suitable for sterilization if the rate of change is less than an empirically-derived rate at which a pre-determined level of sterilization is achieved. The load may then be sterilized.

Advantageously, the pre-determined level of sterilization is a reduction in microorganisms to a level of $10^{-6}$ of the initial level. Preferably, the suitability of the load is determined less than 100 seconds after contacting the load with the germicide vapor or gas. In a preferred embodiment, the rate of change in the concentration is determined as the initial slope of a graph of $\log_x(c/c_0)$ versus time, where x is any number, c is the concentration of the germicide gas or vapor, and $c_0$ is the maximum concentration of the germicide gas or vapor in the sterilization chamber.

Preferably, $\log_x$ is $\log_{10}$ or ln. Advantageously, the germicide gas or vapor is hydrogen peroxide vapor. In a preferred embodiment, the load is contacted with plasma before the load is contacted with hydrogen peroxide vapor. In an embodiment, the load is determined to be unsuitable if the negative of the initial slope is 0.016 $\sec^{-1}$ or greater, where $\log_x$ is ln. Advantageously, the sterilization is aborted if the load is determined to not be suitable. Aborting may be performed by evacuating the sterilization chamber or by generating plasma in the sterilization chamber.

In another embodiment, more germicide gas or vapor may be added into the sterilization chamber, if the load is determined to be unsuitable. Preferably, the germicide gas or vapor is hydrogen peroxide vapor. Advantageously, monitoring can be performed by measuring the concentration of hydrogen peroxide vapor with a spectrometer or by measuring the quantity of heat evolved by a reaction of the hydrogen peroxide vapor with a chemical compound.

Another aspect of the invention involves a method for sterilizing a load with a germicide vapor or gas including placing the load into a sterilization chamber, evacuating the sterilization chamber, contacting the load in the sterilization chamber with germicide vapor or gas, and monitoring the concentration of the germicide vapor or gas in the sterilization chamber as a function of time. The method also includes determining the area under a curve of a graph of c versus time, where c is the concentration of the germicide vapor or gas. The method also includes determining the suitability of the load, where the load is suitable for sterilization if the area is greater than an empirically derived area with which a pre-determined level of sterilization is achieved. The load may then be sterilized.

Preferably, the germicide vapor or gas includes hydrogen peroxide. Advantageously, the area. under the curve is determined from the time of the maximum concentration of the germicide vapor or gas to a time at the end of contacting the load with germicide vapor or gas. In an embodiment, the load is suitable if the area under the curve is greater than 400 mg-sec/L. In a preferred embodiment, the sterilization is aborted, if the load is determined to be not suitable. Alternatively, more germicide gas or vapor may be added if the load is determined to be not suitable.

Another aspect of the invention involves a method for sterilizing a load with a germicide vapor or gas including placing the load into a sterilization chamber, evacuating the sterilization chamber, contacting the load in the sterilization chamber with germicide vapor or gas, and determining the concentration of the germicide vapor or gas. The method also includes determining the suitability of the load from the concentration, where the load is suitable for sterilization if the concentration is greater than an empirically derived concentration with which a pre-determined level of sterilization is achieved. The load may then be sterilized.

Preferably, the sterilization is aborted if the load is determined to be not suitable. Alternatively, more germicide gas or vapor may be added if the load is determined to be not suitable. Advantageously, the germicide vapor or gas includes hydrogen peroxide. In a preferred embodiment, the load is suitable for sterilization if the concentration of germicide vapor or gas is 0.47 mg/L or greater.

DETAILED DESCRIPTION OF THE PREFERRED EMBODIMENT

The embodiments of the method of the present invention provide a means for rapidly determining whether a load of medical equipment is suitable for sterilization with a germicide gas or vapor. If the load is not suitable, the sterilization cycle can be aborted before significant amounts of the germicide gas or vapor have been absorbed, decomposed, adsorbed, or condensed on the equipment, reducing the amount of time required to start a new sterilization cycle. Hydrogen peroxide is an exemplary germicide vapor for use in various embodiments of the method of the invention.

Figure 1:
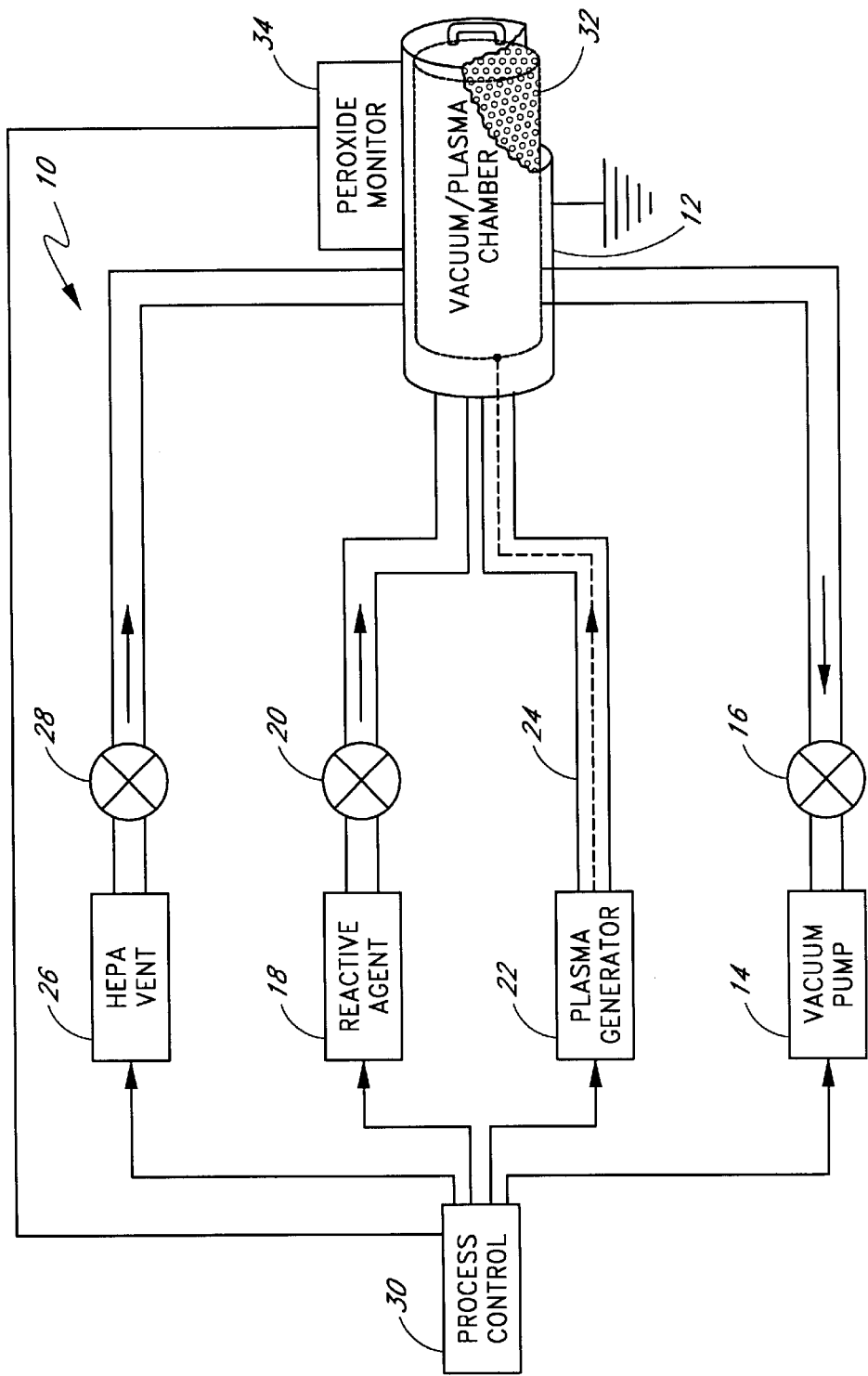
FIG. 1 is a simplified diagram of a sterilization apparatus suitable for use with embodiments of the method of the present invention.

Referring to the drawings, FIG. 1 depicts a sterilizer 10 in block diagram form. The sterilizer 10 and its components and methods of use are described more fully in U.S. Pat. Nos. 4,643,876 and 4,756,882. These patents are incorporated by reference herein. Other sterilizers are suitable for the method of the invention, and the sterilizer 10 of FIG. 1 is not meant to be limiting to the method. Many different frequencies and configurations can be used to generate the gas plasma. The gas plasma can be generated inductively or capacitively with an electrode inside or outside the chamber. The gas plasma can also be generated in a separate chamber and directed from the separate chamber to the sterilizer.

The sterilizer 10 includes a vacuum chamber 12, a vacuum pump 14 connected to the vacuum chamber 12 via a line and a valve 16, and a source of suitable reactive agent 18 or vaporizable germicide such as hydrogen peroxide connected to the vacuum chamber 12 by a line having a valve 20 therein. The sterilizer 10 also includes a plasma generator 22, such as an RF generator, electrically connected to an electrode 32 inside the vacuum chamber 12 by a suitable coupling 24, as well as a HEPA (High Efficiency Particulate Filtered Air) vent 26 connected to the vacuum chamber via a line with a valve 28. A process control logic 30, preferably a programmable computer, is connected to each of the components which are connected to the vacuum chamber 12. The process control logic 30 directs the operation of each of the components connected to the vacuum chamber at the appropriate time to effectuate the sterilization operation.

The vacuum chamber 12 contains the objects to be sterilized and is sufficiently gas-tight to support a vacuum of 300 mTorr or less. Inside the chamber 12 is an RF antenna, or electrode array 32 to which the RF energy from the RF generator 22 is supplied through the coupling 24. A peroxide monitor 34 is fluidly connected to the vacuum chamber 12 and to the process control logic 30.

The peroxide monitor 34 can be any device which is capable of measuring the concentration of hydrogen peroxide in the vapor phase in the vacuum chamber 12. Some methods of measuring the concentration of hydrogen peroxide in the vacuum chamber 12 include pressure measurement, measurement of the hydrogen peroxide absorption in the near infrared (NIR) region, and measurement of the hydrogen peroxide absorption in the ultraviolet (UV) region. Other forms of monitoring the hydrogen peroxide such as measuring the dew point inside the vacuum chamber 12 with the apparatus described by Cummings (U.S. Pat. No. 4,843,867) may also be used in embodiments of the method of the invention. Copending application Ser.

No. 09/468,767, herein incorporated by reference, discloses determining the concentration of hydrogen peroxide by measuring the amount of heat generated from the reaction of hydrogen peroxide with a compound such as potassium iodide, magnesium chloride, catalase, or iron (II) acetate. The concentration of hydrogen peroxide can be determined from the amount of heat evolved and the known heat of reaction. Determining the concentration of hydrogen peroxide vapor by measuring the amount of heat which is generated is also a suitable method for use in embodiments of the invention. The embodiments of the method of the invention are not to be limited by the method of measuring the hydrogen peroxide concentration in the vapor phase in the vacuum chamber 12.

In an exemplary embodiment, the concentration of hydrogen peroxide in the vacuum chamber 12 is monitored by measuring the absorption of vapor phase hydrogen peroxide in the ultraviolet region.

The peroxide monitor 34 may be mounted inside or outside the vacuum chamber 12. Further, portions of the peroxide monitor 34 may be mounted inside the vacuum chamber 12 with other portions of the peroxide monitor 34 being mounted outside the vacuum chamber 12.

In some embodiments, the peroxide monitor 34 may be movable within the vacuum chamber. If the peroxide monitor 34 is movable, it can be placed on a shelf on which medical devices to be sterilized are placed. In another embodiment, the movable peroxide monitor 34 may be placed on a shelf on which the load or a tray or trays of medical devices to sterilized are placed. In another embodiment, the movable peroxide monitor 34 may be placed inside a container which holds medical devices to be sterilized.

If the method of the embodiments of the invention is applied to germicide gas or vapor other than hydrogen peroxide, the peroxide monitor 34 may be any device that is capable of measuring the concentration of the germicide gas or vapor which is utilized.

Figure 2:
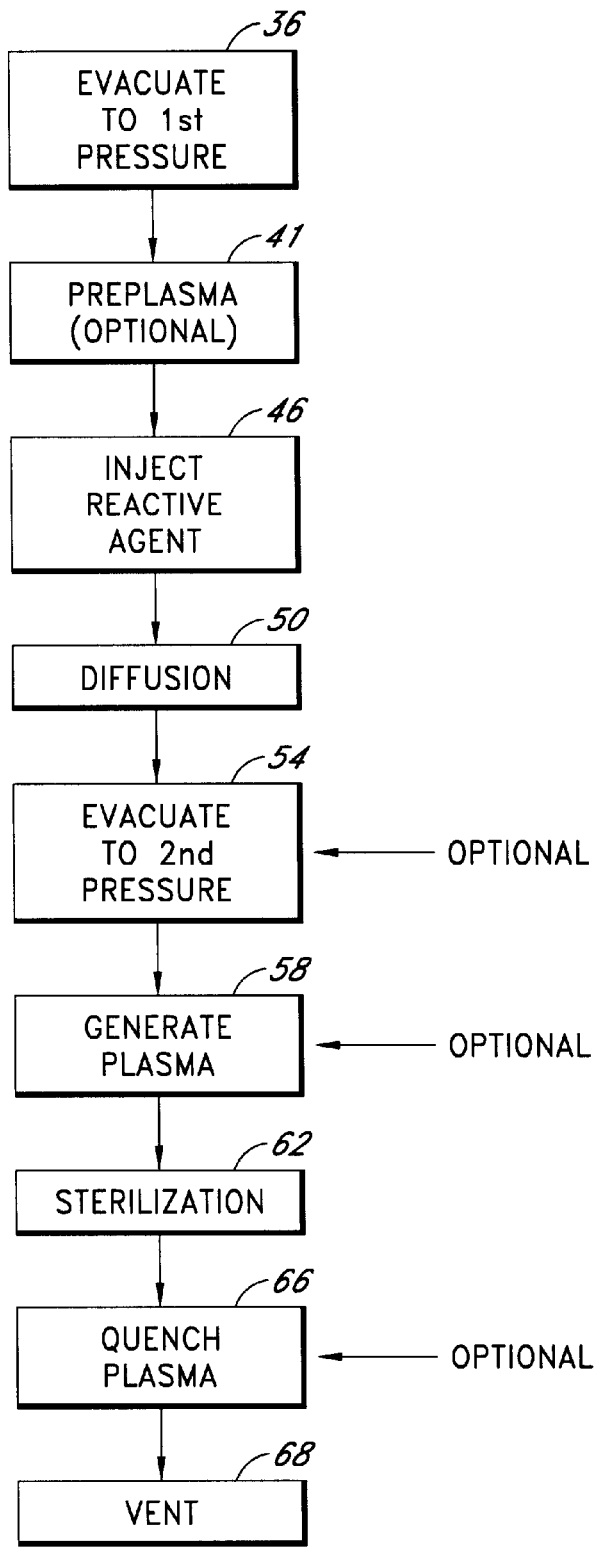
FIG. 2 is a block diagram of a plasma sterilization process.
Figure 3:
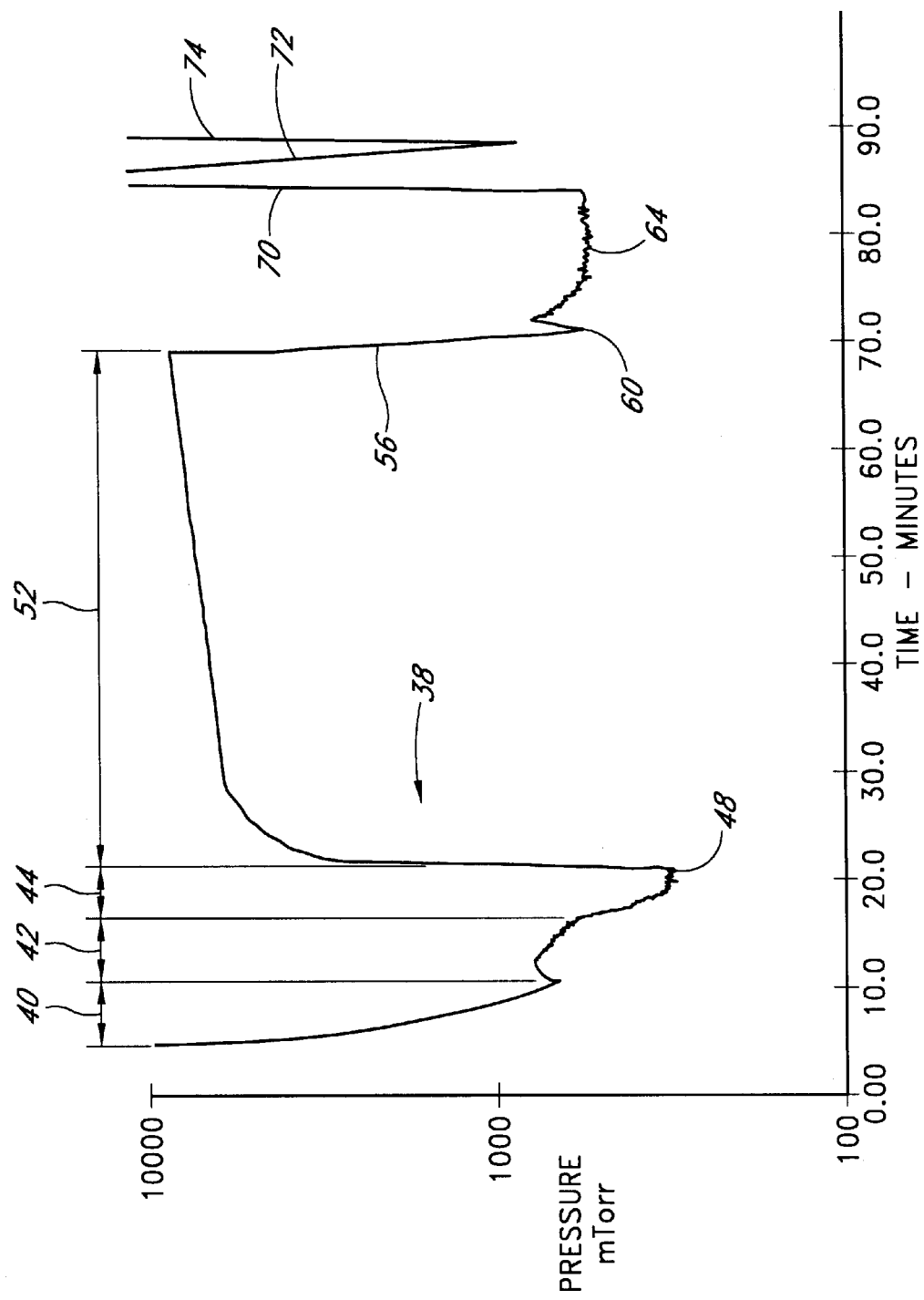
FIG. 3 is a curve showing the pressure inside the sterilization chamber during a plasma sterilization process.

Operation of the sterilizer 10 with the STERRAD sterilization process is described in FIGS. 2–3, where FIG. 2 is a block diagram showing the sequence of operations in the sterilizer 10, and FIG. 3 illustrates the pressure inside the vacuum chamber 12 as a function of time. Although the sterilization process shown in FIGS. 2 and 3 is an exemplary sterilization process, the method of various embodiments of the invention is also suitable for application in other sterilization processes.

After the objects to be sterilized have been placed in the vacuum chamber 12 and the chamber 12 has been sealed, the process control logic 30 engages the vacuum pump 14 and valve 16 to evacuate the vacuum chamber 12, step 36 in FIG. 2. The pressure in the vacuum chamber 12 during the sterilization process is shown qualitatively as curve 38 in FIG. 3. The pressure curve during the evacuation step 36 is shown as curve 40 in FIG. 3. The chamber is preferably evacuated to a pressure of less than or equal to 5000 mTorr, more preferably 200–2000 mTorr, and most preferably about 300–1500 mTorr.

When the desired pressure has been reached, in an exemplary embodiment, the process control logic 30 transmits a signal to the RF generator 22 to energize the electrode 32 within the chamber 12. This action causes a gas plasma to be created inside the chamber in a pre-injection plasma step, step 41 of FIG. 2. Because the articles to be sterilized are loaded into the chamber in the presence of air and moisture, the residual gases which form the plasma in the pre-injection plasma are mainly air and moisture. Although the pre-injection plasma step 41 is optional, it is generally preferred to perform the pre-injection plasma step 41.

As described in U.S. Pat. Nos. 5,656,238 and 6,060,019, hereby incorporated by reference, energy is transferred to condensed water in the chamber during the pre-injection plasma step 41, thereby aiding the drying of the vacuum chamber 12 and the equipment in the chamber. While plasma is being generated, the vacuum pump 14 remains engaged to further evacuate the chamber and to remove residual gases and moisture from the chamber. The pressure in the vacuum chamber in the pre-injection plasma step 41 is shown as curve 42 in FIG. 3. During the pre-injection plasma step 41, the pressure in the vacuum chamber 12 rises due to vapor generation. After a period of time, approximately 0–60 minutes, the RF generator 22 is turned off. If the period of time is 0, the optional pre-injection plasma step is omitted.

At this point in the process, the evacuation is continued with no plasma. The pressure curve in the vacuum chamber after the RF generator 22 is turned off is shown as curve 44 in FIG. 3. In an exemplary embodiment, evacuation continues until a pressure of approximately 300 mTorr is attained.

When a desired vacuum threshold has been reached, the reactive sterilization agent 18 is injected during step 46 of FIG. 2. The injection of the sterilization agent 18 during step 46 causes the pressure inside the vacuum chamber 12 to rapidly rise. In an exemplary embodiment, the pressure may rise to a level of 5000 mTorr or more. The start of the injection phase is shown as 48 in FIG. 3. The injection phase takes approximately 6 minutes. After the sterilization agent 18 is injected into the vacuum chamber 12, it is allowed to diffuse completely and evenly throughout the vacuum chamber 12 during step 50 of FIG. 2. This step typically lasts approximately 1–45 minutes, at which time the reactive agent or sterilization agent 18 should be substantially in equilibrium inside the vacuum chamber 12. The pressure curve in the vacuum chamber 12 during the injection phase and diffusion phases, steps 46 and 50 of FIG. 2, is shown as curve 52 in FIG. 3.

At the end of the diffusion period, the process control logic 30 again engages the vacuum pump 14 and opens the valve 16 to pump down the vacuum chamber 12 to a vacuum of approximately 400–2000 mTorr during step 54 of FIG. 2. The pressure in the vacuum chamber 12 during step 54 is shown as curve 56 in FIG. 3. When the pressure inside the vacuum chamber 12 has reached approximately 400–2000 mTorr, the process control logic 30 commands the RF generator 22 to generate an RF signal which is transmitted to the electrode 32. This action causes a gas plasma to be created inside the vacuum chamber 12 during step 58 of FIG. 2. The plasma generation step 58 is also called the post-injection plasma step. The components forming the plasma in the post-injection plasma step are dissociation species of the reactive agent 18, for example, hydrogen peroxide, as well as molecules of residual gas remaining in the vacuum chamber 12.

The start of step 58 is shown as 60 in FIG. 3. Generating the plasma causes a brief rise in pressure in the vacuum chamber 12, as indicated by the pressure curve after 60 in FIG. 3. The electrode 32 remains energized for approximately 1–15 minutes during the sterilization step 62 of FIG. 2. The plasma and hydrogen peroxide can effectively destroy any pathogens present in the vacuum chamber 12. The pressure in the vacuum chamber 12 during the post-injection plasma step, steps 58 and 62 of FIG. 2, is shown as curve 64 in FIG. 3. The majority of the sterilization step 62 is conducted at a relatively constant pressure of approximately 400–2000 mTorr, as shown by the remainder of pressure curve 64. At the end of the sterilization step 62, the current to the RF generator is stopped, quenching the plasma, step 66 of FIG. 2.

After the sterilization process is complete, the vacuum chamber 12 is vented through the HEPA vent 26 during the venting step 68 of FIG. 2. The pressure in the sterilization chamber 12 during the venting step 68 is shown as curve 70 of FIG. 3. The vacuum chamber 12 is then evacuated to remove any remaining reactive agent 18 or sterilizing agent which may be present in the vacuum chamber 12. The vacuum chamber 12 is evacuated to a pressure of approximately 300–1000 mTorr, as shown by curve 72 of FIG. 3. Following this step, the vacuum chamber is vented again to atmospheric pressure through the HEPA vent 26, as shown by curve 74 in FIG. 3. The sterilized articles are then removed from the sterilization chamber 12.

Figure 4:
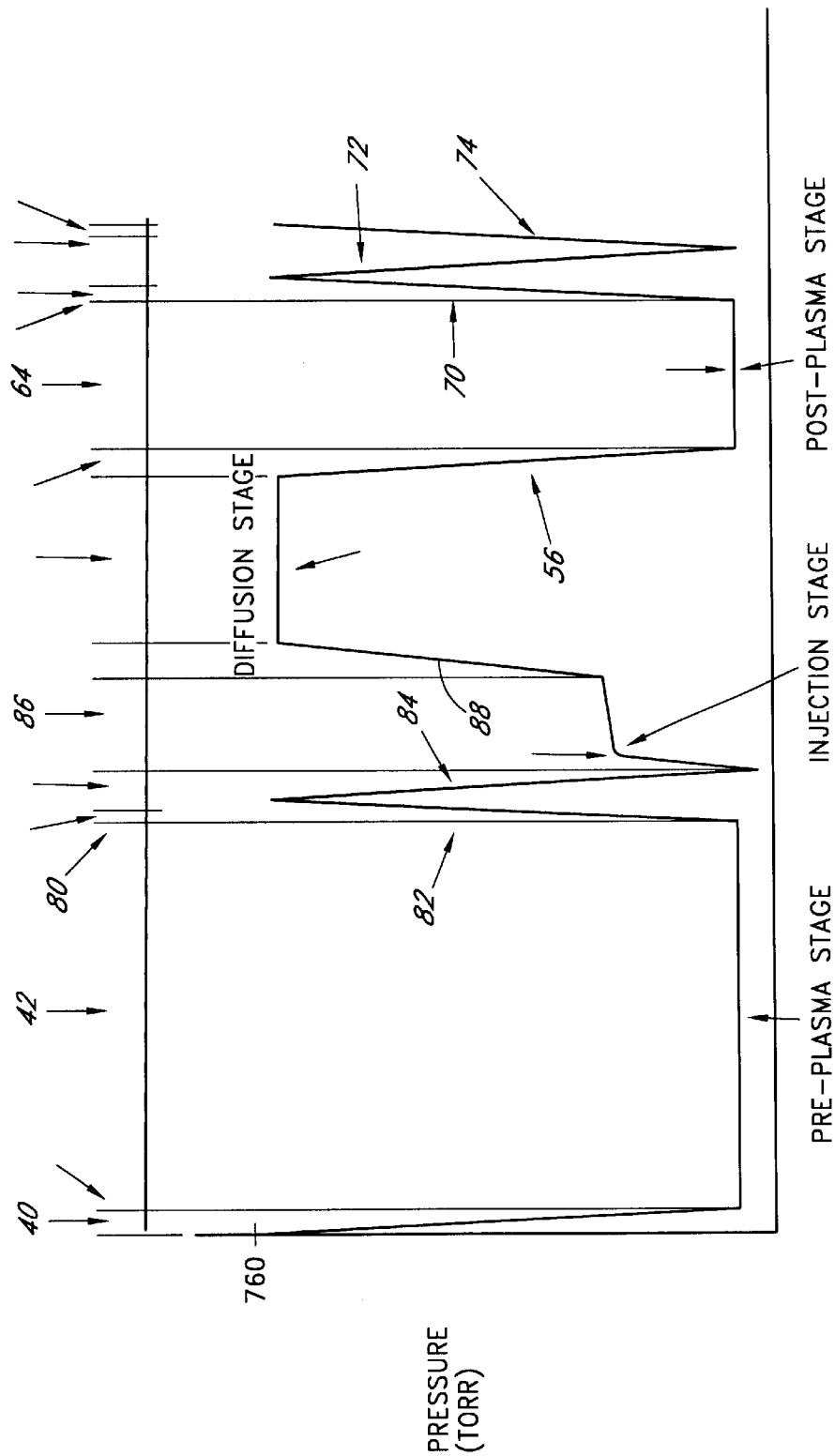
FIG. 4 is a curve showing the pressure inside the sterilization chamber during an alternative plasma sterilization process.

FIG. 4 shows an alternative sterilization cycle, the STERRAD® 200 cycle. Please note that the times in FIG. 4 are not drawn to scale, and the curve is meant to be qualitative only. The STERRAD 200 cycle is very similar to the previously described STERRAD cycle with two exceptions which are described in detail below. In the STERRAD 200 cycle, after the pre-injection plasma step 41, shown as curve 42 in FIG. 4, the plasma is shut off at 80 in FIG. 4. After the plasma is shut off, the sterilization chamber 12 is vented to approximately atmospheric pressure. The pressure curve in the chamber during the venting is shown as curve 82 in FIG. 4. Venting after the pre-plasma step 41 is believed to transfer heat from the electrode 32 and the walls of the chamber 12 to the load, warming the load, improving the effectiveness of the sterilization. The first major difference between the normal STERRAD cycle and the STERRAD 200 cycle is therefore that the sterilization chamber 12 is vented after the pre-injection plasma step.

In an exemplary embodiment, the sterilization chamber 12 is maintained at approximately atmospheric pressure only briefly after the venting. In alternative embodiments, the sterilization chamber 12 is maintained at atmospheric pressure for less than 10 minutes after venting, more preferably for less than 5 minutes after venting, and most preferably for less than 1 minute after venting.

After venting, the sterilization chamber 12 is evacuated again. The pressure in the sterilization chamber 12 during the evacuating step after venting is shown as curve 84 in FIG. 4. The chamber 12 is evacuated to a pressure of less than 5000 mTorr, more preferably 200 to 2000 mTorr, and most preferably 300 to 1500 mTorr. After the pressure in the chamber 12 has reached the desired pressure, hydrogen peroxide is injected into the sterilization chamber 12 during the injection stage. The pressure in the chamber 12 during the injection stage is shown as curve 86 in FIG. 4. The injection takes less than 60 minutes, more preferably less than 20 minutes, and most preferably less than 10 minutes.

In the STERRAD 200 cycle, the chamber 12 is preferably vented after the injection stage. The pressure in the chamber 12 during the venting is shown as 88 in FIG. 4. Venting the sterilization chamber 12 after venting is believed to help to push the hydrogen peroxide vapor into the interior of lumens and other diffusion-restricted devices, improving the sterilization of the diffusion-restricted areas. The chamber 12 is preferably vented to approximately atmospheric pressure.

After venting the hydrogen peroxide is allowed to diffuse for up to 60 minutes, more preferably for 0 to 10 minutes, and most preferably for 0 to 5 minutes. Venting the chamber 12 after the injection step and during the diffusion step is the second way in which the STERRAD 200 cycle differs from the normal STERRAD cycle.

After the chamber is vented following injection of hydrogen peroxide, the STERRAD 200 cycle is the same as the normal STERRAD cycle. The chamber 12 is evacuated as in step 54 of FIG. 2, gas plasma is generated inside the chamber 12 and the sterilization is completed at step 62 of FIG. 2. The chamber 12 is vented during the venting step 68, the chamber is evacuated again, the chamber is vented to atmospheric pressure, and the sterilized articles are removed from the sterilization chamber 12.

The STERRAD 200 cycle and the normal STERRAD cycle therefore differ in that in the STERRAD 200 cycle the chamber is vented after the pre-injection plasma step and again after injection of the hydrogen peroxide.

No matter what sterilization cycle and reactive agent 18 is utilized, in order for the sterilization process to be effective, the concentration of reactive agent 18 in the vacuum chamber 12 must be sufficiently high to cause sterilization. In an exemplary embodiment, the reactive agent 18 is hydrogen peroxide. Even if the concentration of hydrogen peroxide in the vacuum chamber 12 immediately after injection is high enough to be effective for sterilization, the hydrogen peroxide vapor can be removed from the sterilization chamber 12 through a variety of processes including condensation, absorption, adsorption, and decomposition. If enough hydrogen peroxide is removed from the vapor phase, there may not be enough to cause effective sterilization of the load in the chamber. If it can be rapidly determined that the load in the sterilization chamber 12 is decomposing, absorbing, adsorbing, or condensing significant amounts of hydrogen peroxide, the sterilization cycle can be aborted so that a new cycle can be initiated before large amounts of time are wasted continuing an ineffective cycle.

Further, if the equipment in the vacuum chamber 12 adsorbs, absorbs, or condenses significant amounts of hydrogen peroxide or other vaporizable germicide, it can take a long period of time to remove the germicide. It is generally preferred that the adsorbed, absorbed, or condensed hydrogen peroxide or other vaporizable germicide be removed from the equipment before an operator unloads the equipment from the vacuum chamber 12 for safety considerations. Being able to rapidly determine whether the equipment in the load to be sterilized is absorbing, adsorbing, condensing, or decomposing the hydrogen peroxide or other vaporizable germicide would therefore save a large amount of time by allowing the run to be aborted before the equipment absorbs, adsorbs, or condenses significant quantities of germicide. Removing small amounts of hydrogen peroxide or vaporizable germicide can be done rapidly.

Experimental Conditions

A series of experiments were run in a STERRAD® 200 Sterilizer, a sterilization apparatus with a vacuum chamber about 270 liters in size, to determine parameters for assessing the suitability of a load for sterilization with hydrogen peroxide. The experiments were performed with the STERRAD 200 cycle, shown in FIG. 4. The sterilization process was run under the following conditions:

TABLE 1

Process Variables for Sterilization Runs

| Process Variable | Nominal Value |
| --- | --- |
| Pre-injection Plasma Time, Min. | 20 |
| Pre-injection Plasma Pressure, mTorr | 300, 600 |
| Chamber Temperature, ° C. | 45 |
| Injection Pressure, mTorr | 600 |
| Vaporizer/Tubes Temperature, ° C. | 65 |
| Peroxide Injection, mg/L | 8.6, 9.3 |
| Injection Time, Min. | 6 |
| Diffusion Time, Min. | 2 |
| Post-injection Plasma Time, Min. | 2 |
| Post injection Plasma Pressure, mTorr. | 600 |
| Pre-Injection Plasma Power, Watts | 460 |
| Post-Injection Plasma Power, Watts | 380, 440, 450 |
| Initial Load/Cart Temperature, ° C. | 20 |

The pressure in the chamber during the pre-injection plasma step 41 was either 300 or 600 mTorr. The effectiveness of the sterilization has been found to not significantly depend on the pre-injection plasma pressure, at least within this pressure range. The hydrogen peroxide injection amount was either 8.6 or 9.3 mg/L. The sterilization results are not significantly dependent on the amount of hydrogen peroxide as long as the hydrogen peroxide injection is at least 8.6 mg/L. Finally, the post-injection plasma power was in the range of 380–450 watts. The sterilization results do not significantly vary with the post-injection plasma power in this power range.

The concentration of vapor phase hydrogen peroxide in the chamber was measured as a function of time by measuring the absorbance of the hydrogen peroxide in the vapor phase of the sterilization chamber with an ultraviolet spectrometer and a mercury vapor lamp source, where the optical path of the ultraviolet spectrometer was inside the vacuum chamber. The absorbance of the hydrogen peroxide was measured at 254 nm, and the concentration of hydrogen peroxide was determined by comparing to a calibration plot of absorbance versus hydrogen peroxide concentration.

Types of Loads Evaluated

Sterilization experiments were carried out on four different types of loads:

1. Validation load—The validation load was an assembly of commonly used medical devices which was chosen as a standard. The validation load is a load which does not absorb, adsorb, or decompose significant amounts of hydrogen peroxide. The validation load is a "no problem" load in which no sterilization runs are expected to be aborted under the normal operating conditions.

2. Heavy load—The heavy load was a validation load with the addition of defibrillator paddles and defibrillator cables. In some of the heavy loads, additional challenges to sterilization were added, such as a piece of filter paper, a silicone mat, or brass strips. The filter paper and the silicone mat absorb moderate amounts of hydrogen peroxide. The brass strips decompose hydrogen peroxide. The heavy load was designed to be a moderately difficult load.

3. Heavy new towel—The heavy new towel load was the heavy load with the addition of a new cloth towel. The new cloth towel is made of cotton, a material which absorbs hydrogen peroxide. The new cloth towel was cut into pieces, and a piece of the new cloth towel was placed into each of the trays of equipment.

4. Heavy old towel—The heavy old towel load was the heavy load together with a cloth towel which had been washed several times. The towel was cut into pieces, and a piece of the old towel was placed into each of the trays of equipment. Washing the cloth towel has been found to increase the amount of hydrogen peroxide which is absorbed by the towel.

Experimental Results

The trays containing the inoculated coupons and the various loads were wrapped with sterilization wrap and sealed with sterilization tape. The trays were then placed into the chamber and treated under the sterilization conditions shown in Table 1. The hydrogen peroxide was injected into the sterilization chamber in two consecutive injections of equal size. The hydrogen peroxide which was injected was 59 weight % aqueous hydrogen peroxide. The mg/L of hydrogen peroxide was calculated on the basis of pure hydrogen peroxide.

The effectiveness of the sterilization process was determined by placing stainless steel coupons inoculated with >$10^6$ *Bacillus stearothermophilus* spores as biological indicators (BI's) into 3 mm×400 mm stainless steel lumens. The lumens were placed into double-wrapped sterilizer trays with the loads of medical instruments to be sterilized. At the end of the cycle, the BIs were recovered from the lumens, placed into tubes of TSB (Trypticase soy broth) medium and incubated at 55–60° C. for 14 days. The biological activity was then determined.

The concentration of vapor phase hydrogen peroxide in the chamber was monitored with the ultraviolet peroxide monitor as a function of time. The pressure inside the chamber was also monitored as a function of time. After the completion of the sterilization cycle, the chamber was vented, the equipment was removed, and the inoculated coupons were tested for growth in the medium. The data on the hydrogen peroxide concentration as a function of time were analyzed in several ways. The sterilization results and the summary of the various methods of analyzing the hydrogen concentration data are shown in Table 2 below.

TABLE 2

Summary of Results of Modeling of Hydrogen Peroxide Monitoring

| Run | Load | Fraction Positive BIs | $C_f$ (mg/L) | $C_f/C_o$ | -ln ($C_f/C_o$) | - Initial slope, k, sec$^{-1}$ | Area under C versus t curve | Pressure ($P_o$) Torr | Pressure ($P_f$) Torr |
| --- | --- | --- | --- | --- | --- | --- | --- | --- | --- |
| | | | | Group 1 | | | | | |
| 34-1-1 | Validation | 0/10 | 0.89 | 0.23 | 1.46 | 0.011 | 509 | 7.16 | 7.42 |
| 34-1-2 | Validation | 0/10 | 0.86 | 0.23 | 1.49 | 0.011 | 498 | 7.11 | 7.07 |

TABLE 2-continued

Summary of Results of Modeling of Hydrogen Peroxide Monitoring

| Run | Load | Fraction Positive | $C_f$ (mg/L) BIs | $C_f/C_o$ | $-\ln(C_f/C_o)$ | - Initial slope, k, sec$^{-1}$ | Area under C versus t curve | Pressure ($P_o$) Torr | Pressure ($P_f$) Torr |
|---|---|---|---|---|---|---|---|---|---|
| 34-1-3 | Validation | 0/10 | 0.88 | 0.25 | 1.37 | 0.010 | 493 | 7.18 | 7.51 |
| 34-1-4 | Validation | 0/10 | 0.92 | 0.28 | 1.28 | 0.009 | 501 | 7.47 | 7.69 |
| 34-1-5 | Validation | 0/10 | 0.94 | 0.24 | 1.42 | 0.010 | 534 | 7.55 | 7.46 |
| 34-1-6 | Validation | 0/10 | 1.02 | 0.30 | 1.20 | 0.008 | 536 | 7.56 | 7.90 |
| | | | | Group 2 | | | | | |
| xheav | Heavy | 1/10 | 0.46 | 0.12 | 2.12 | 0.016 | 398 | 7.43 | 6.59 |
| xheav1 | Heavy, 1 filter | 0/10 | 0.50 | 0.13 | 2.05 | 0.016 | 392 | 7.30 | 6.69 |
| xheav2 | Heavy, 2 filters | 0/10 | 0.46 | 0.11 | 2.22 | 0.017 | 373 | 7.83 | 6.71 |
| 46-6-2 | Heavy, mat | 0/10 | 0.47 | 0.12 | 2.11 | 0.013 | 429 | 8.05 | 8.07 |
| 46-6-3 | Heavy, mat | 0/10 | 0.49 | 0.13 | 2.06 | 0.013 | 439 | 8.26 | 8.06 |
| 91-10 | Heavy, brass | 0/10 | 0.51 | 0.16 | 1.80 | 0.012 | 364 | 7.13 | 6.24 |
| | | | | Group 3 | | | | | |
| 91-11 | Heavy, 1 new towel | 6/10 | 0.12 | 0.04 | 3.14 | 0.026 | 156 | 5.87 | 3.89 |
| 91-12 | Heavy, 6/8 towel | 3/10 | 0.24 | 0.08 | 2.59 | 0.019 | 246 | 6.10 | 4.16 |
| 91-13 | Heavy, 2 new towels | 5/10 | 0.08 | 0.03 | 3.48 | 0.028 | 129 | 5.02 | 3.01 |
| | | | | Group 4 | | | | | |
| c12038 | Heavy, old towel | 10/10 | 0.001 | 0.0004 | 7.71 | 0.039 | 76 | 5.88 | 4.27 |
| c1238r1 | Heavy 1 old towel | 10/10 | 0.0002 | 0.0009 | 6.94 | 0.025 | 118 | 4.88 | 3.34 |
| | | | | Group 5 | | | | | |
| 1012991 | Validation | 0/12 | | | | 0.012 | | | |
| 1012992 | Validation | 0/12 | | | | 0.009 | | | |
| 1012993 | Validation | 0/12 | | | | 0.010 | | | |
| 1013991 | Validation | 0/12 | | | | 0.008 | | | |
| 1013992 | Validation | 0/12 | | | | 0.010 | | | |
| 1013993 | Validation | 0/12 | | | | 0.008 | | | |
| | | | | Group 6 | | | | | |
| 1123991 | Validation | 0/12 | | | | 0.013 | | | |
| 1123992 | Validation | 0/12 | | | | 0.015 | | | |
| 1123993 | Validation | 0/12 | | | | 0.016 | | | |
| 1123994 | Validation | 0/12 | | | | 0.017 | | | |
| 1123995 | Validation | 0/12 | | | | 0.013 | | | |
| 1124991 | Validation | 0/12 | | | | 0.023 | | | |
| 122991 | Validation | 0/12 | | | | 0.017 | | | |
| 123991 | Validation | 0/12 | | | | 0.013 | | | |
| 127991 | Validation | 0/12 | | | | 0.017 | | | |
| 127992 | Validation | 0/12 | | | | 0.021 | | | |
| 128991 | Validation | 0/12 | | | | 0.015 | | | |
| | | | | Group 7 | | | | | |
| 128991 | Valid, 1 towel | 0/12 | | | | 0.021 | | | |
| 128992 | Valid, 1 towel | 0/12 | | | | 0.018 | | | |
| 128993 | Valid, 1 towel | 0/12 | | | | 0.019 | | | |
| 128994 | Valid, 1 towel | 1/12 | | | | 0.018 | | | |
| 128995 | Valid, 1 towel | 0/12 | | | | 0.021 | | | |
| 128996 | Valid, 1 towel | 3/12 | | | | 0.020 | | | |
| | | | | Group 8 | | | | | |
| 1215991 | Valid, 2 towel | 0/12 | | | | 0.028 | | | |
| 1215992 | Valid, 2 towel | 0/12 | | | | 0.027 | | | |
| 1215993 | Valid, 2 towel | 0/12 | | | | 0.029 | | | |
| 1215994 | Valid, 2 towel | 0/12 | | | | 0.028 | | | |
| 1216991 | Valid, 2 towel | 3/12 | | | | 0.028 | | | |
| 1216992 | Valid, 2 towel | 0/12 | | | | 0.028 | | | |

The definition of the terms $C_f$, $C_0$, $P_0$, and $P_f$ will be described in more detail below.

The runs are grouped in Table 2 by the type of load and by the run conditions. Table 3 below summarizes the information on the load types and the run conditions for the various groups of sterilization runs.

TABLE 3

Group Variation in Type of Load and Sterilization Conditions

| Group | Load | mg/L $H_2O_2$ Injected | Number of Trays | Initial Load Temperature | Pre-Plasma, Minutes |
|---|---|---|---|---|---|
| 1 | Validation | 8.6 (3 runs) 9.3 (3 runs) | 6 | | 20 |
| 2 | Heavy | 8.6 | 6 | | 20 |
| 3 | Heavy, 6/8, 1 or 2 new towels | 8.6 | 6 | | 20 |
| 4 | Heavy, 1 old towel | 8.6 | 6 | | 20 |
| 5 | Validation | 9.3 | 4 | 5° C. | 15 |
| 6 | Validation | 9.3 | 4 | 5° C. | None |
| 7 | Validation, 1 towel | 9.3 | 4 | | 20 |
| 8 | Validation, 2 towels | 9.3 | 4 | | 20 |

The Groups varied in the types of loads, the concentration of hydrogen peroxide, the initial temperatures of the loads, the number of trays in the load, and the length of the pre-injection plasma treatment.

In run 91-12 of Group 3, a towel having a size of 16×25 inches was cut into 8 pieces of equal size. One piece of the towel was placed into the tray in run 91-12. The tray in this run therefore contained ⅛ of a towel. In the other runs in Groups 3 and 4, the towels were cut into 6 pieces of equal size, and one piece of the towel was placed into each of the 6 trays. Similarly, in the runs in Groups 7 and 8, the towels were cut into 4 pieces of equal size, and one piece of towel was placed into each of the 4 trays.

Sterilization Results

The sterilization results are summarized in Table 2. In general, the sterilization results correlate well with the type of load which was placed into the sterilization chamber. Thus, the runs in Groups 1, 5, and 6 of Table 2 all used validation loads, loads which are less challenging than the loads in the other groups. All of the Biological Indicators in the runs with the validation loads were negative for growth.

In the runs in Groups 5 and 6 with validation loads, the loads were initially cooled to 5° C. to simulate a load which had been stored in a refrigerated hospital preparation room and placed immediately into the sterilization chamber. The cool load condenses some of the hydrogen peroxide, removing some of the hydrogen peroxide from the vapor phase in the chamber, at least at the beginning of the cycle. All of the Biological Indicators in the runs in Groups 5 and 6 with the cool loads were negative for growth. The sterilizations with the cool validation loads were therefore effective in spite of the low temperature of the loads.

In the runs in Group 5, the cool load was exposed to 15 minutes of pre-plasma. The pre-plasma, in addition to removing water from the load, also heats the load, counteracting, at least to some extent, the low temperature of the load when loaded into the sterilization chamber. In the runs in Group 6, in contrast, the cool load was not exposed to any pre-plasma. All of the biological indicators were negative, even though the load was not warmed with pre-plasma as in the Group 5 runs.

Turning to the Group 2 runs with the heavy load, the sterilization runs were in the initial quantal region, with one BI which showed growth (positive BI). The Group 3 runs with the heavy load and the new towel were in the mid-quantal, with a significant number of positive BI's. The new towel is made of cellulose, a material which absorbs hydrogen peroxide. The BIs in the Group 4 runs with the heavy load and the old towel were all positive. It has been found that the old towel, a towel which has been washed several times, absorbs more hydrogen peroxide than a new towel. The sterilization results for the Group 3 and Group 4 runs are consistent with the fact that the old towel of the Group 4 runs absorbs more hydrogen peroxide than the new towel of the Group 3 runs.

Similarly, adding either 1 or 2 towels to the validation loads in the runs in Groups 7 and 8 runs led to a few positive BI's, compared to all negative BI's with the runs in Groups 1, 5, and 6 with validation loads and no towels. The towels absorb hydrogen peroxide, reducing the amount of available hydrogen peroxide in the vapor phase in the chamber during the sterilization process.

The type of load therefore correlates highly with the effectiveness of the sterilization process. If one knew in advance the characteristics of the load, that is whether the load absorbs, adsorbs, condenses, or decomposes hydrogen peroxide, one would be able to determine whether the run should be aborted because of the unfavorable characteristics of the load.

Normally, one does not know in advance whether a load to be sterilized will absorb, adsorb, condense, or decompose hydrogen peroxide. One therefore does not know in advance whether a load will behave like a validation load, a cold load, a heavy load, a heavy new towel load, or a heavy old towel load. If one could quickly determine that the load is unsuitable for sterilization because it absorbs, adsorbs, condenses, or decomposes a significant amount of hydrogen peroxide, the sterilization run could be quickly aborted and the unsuitable material in the load could be removed before starting a new run.

Data Analysis

The concentration of vapor phase hydrogen peroxide in the sterilization chamber was measured as a function of time during the sterilization runs. The data were analyzed in various ways to determine whether a method could be found to quickly determine the suitability of the load for sterilization.

The rate of change of the hydrogen peroxide in the vapor phase can be expressed with the following mass balance equation:

$dc/dt$=mass/volume flow rate in−mass/volume flow rate out−mass/volume rate from reaction, where $dc/dt$ is the time rate of change in hydrogen peroxide concentration in the vapor phase in the chamber, where the mass/volume flow rate in and mass/volume flow rate out=the convective flow rates of hydrogen peroxide into and out of the chamber, and where the mass/volume rate from reaction is the loss of hydrogen peroxide in any form, including condensation, reaction, absorption, adsorption, and decomposition.

The system is treated as a closed system after the hydrogen peroxide is injected. Therefore, the convective flow terms are zero, i.e., the mass flow rate in=mass flow rate out=0. If one assumes that the hydrogen peroxide is injected as a slug at t=0, and that the reaction is first order, $$dc/dt = -kc,$$

where k is the rate constant for loss of hydrogen peroxide from the vapor phase.

The equation can be rearranged and integrated as follows:

$$dc/c = -k\, dt$$

$$\int_{c_0}^{c} d\ln c = \int_{t_0}^{t} -k\, dt$$

$$\ln(c/c_0) = -k(t-t_0)$$

where $c_0$ is the initial concentration of hydrogen peroxide in the vapor phase at initial time $t_0$, and c is the concentration of hydrogen peroxide in the vapor phase at any time t. Dividing the concentration of hydrogen peroxide as a function of time by the initial concentration of hydrogen peroxide normalizes the concentration and makes the term dimensionless.

$$\text{For } t_0 = 0, \ln(c/c_0) = -kt$$

A plot of $\ln(c/c_0)$ versus t will be a straight line with a slope of $-k$, if the rate of hydrogen peroxide loss follows first-order kinetics. A plot of $\log_{10}(c/c_0)$ versus time would also give a straight line of slope $-m$, with $k=2.3\,m$. More generally, a plot of $\log_x(c/c_0)$ versus time will be a straight line with a slope depending on x, where x can be any number.

Graphs of Hydrogen Peroxide Loss Versus Time

Figure 5:
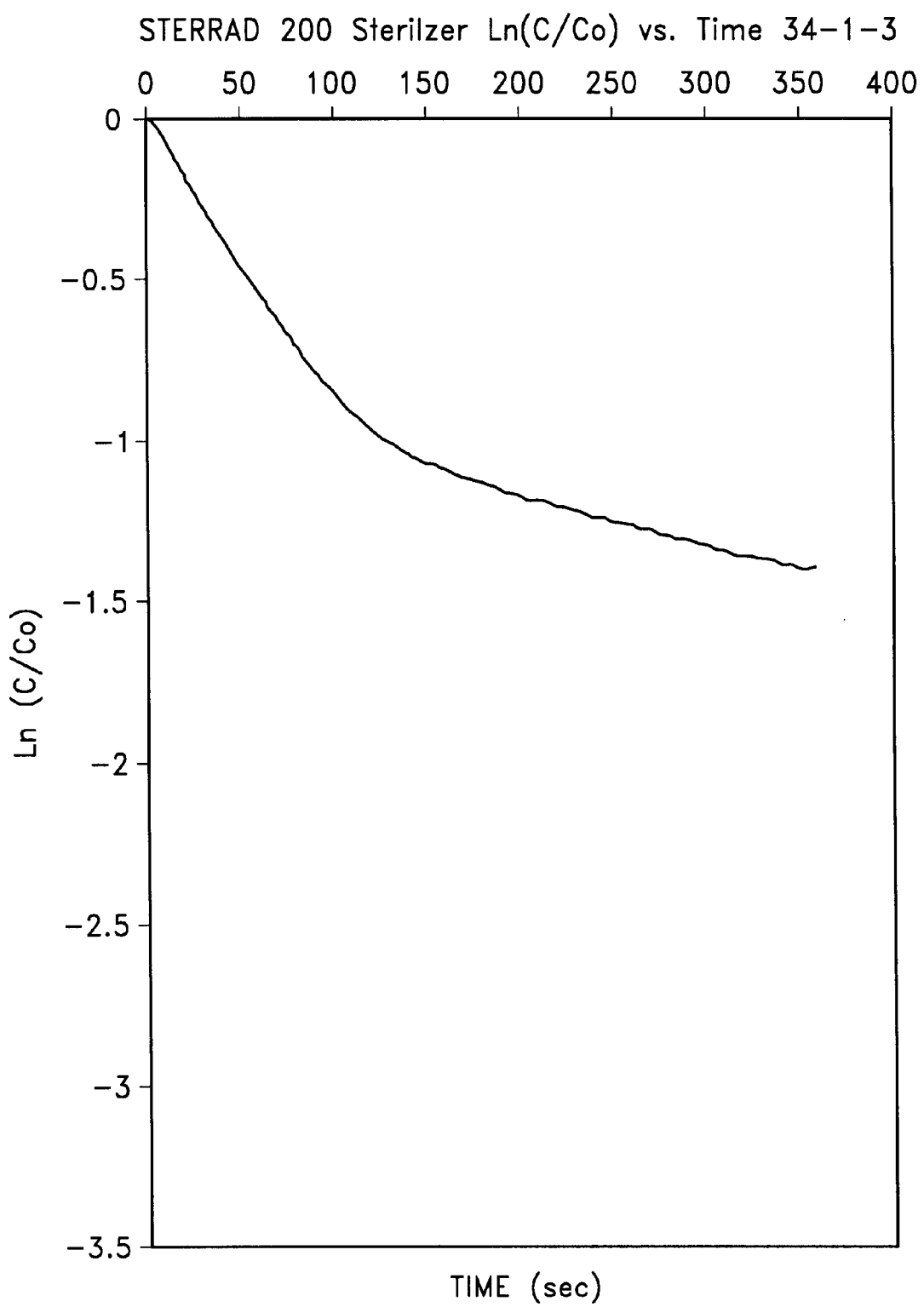
FIG. 5 is a graph of $\ln(c/c_0)$ versus time for a sterilization experiment with a validation load, where c is the hydrogen peroxide concentration at any time point and $c_0$ is the maximum concentration of hydrogen peroxide.
Figure 6:
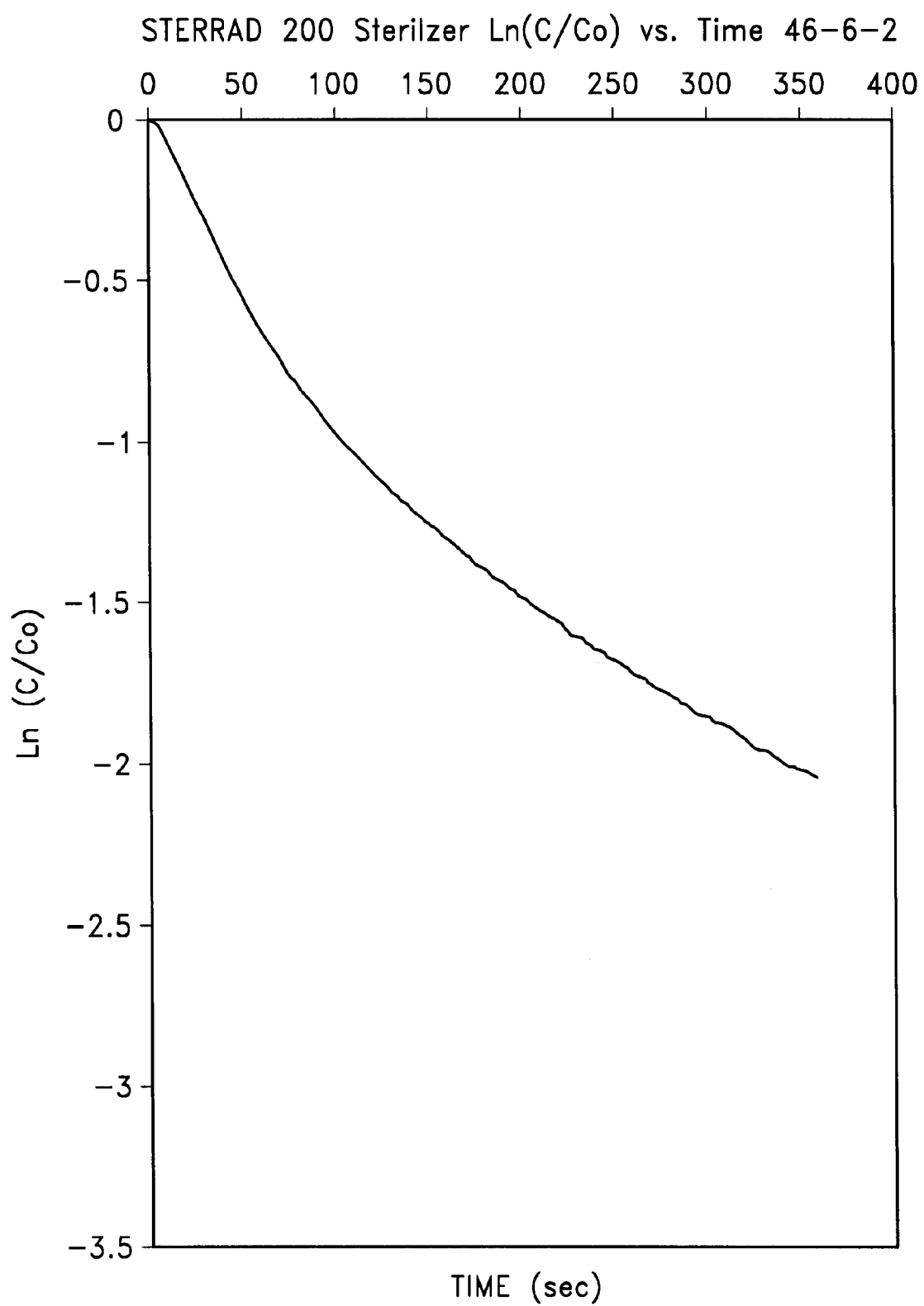
FIG. 6 is a graph of $\ln(c/c_0)$ versus time of the hydrogen peroxide concentration for a sterilization experiment with a heavy load during the injection step.
Figure 7:
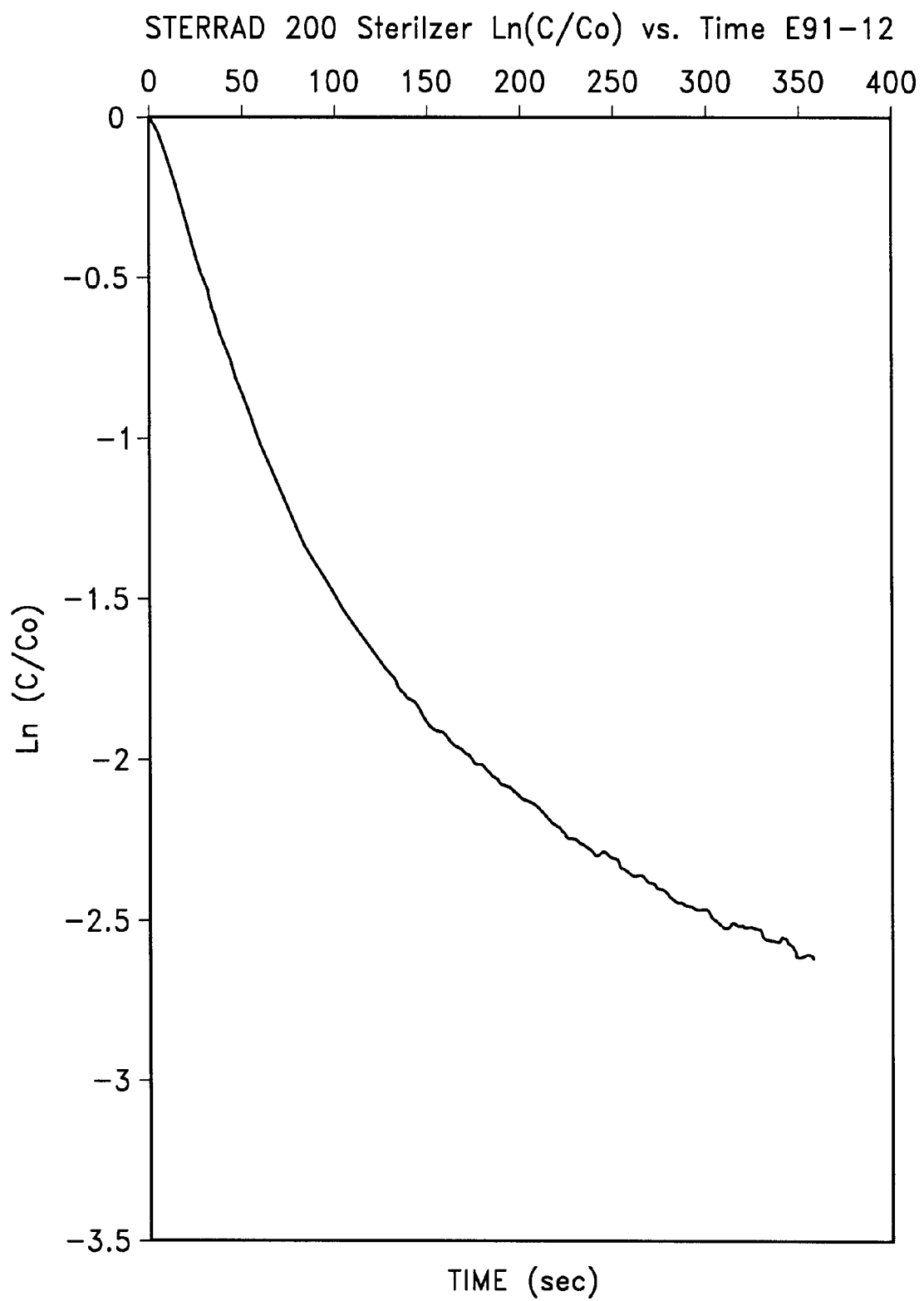
FIG. 7 is a graph of $\ln(c/c_0)$ versus time of the hydrogen peroxide concentration for a sterilization experiment with a heavy load containing an absorbent material, such as a cotton towel.
Figure 8:
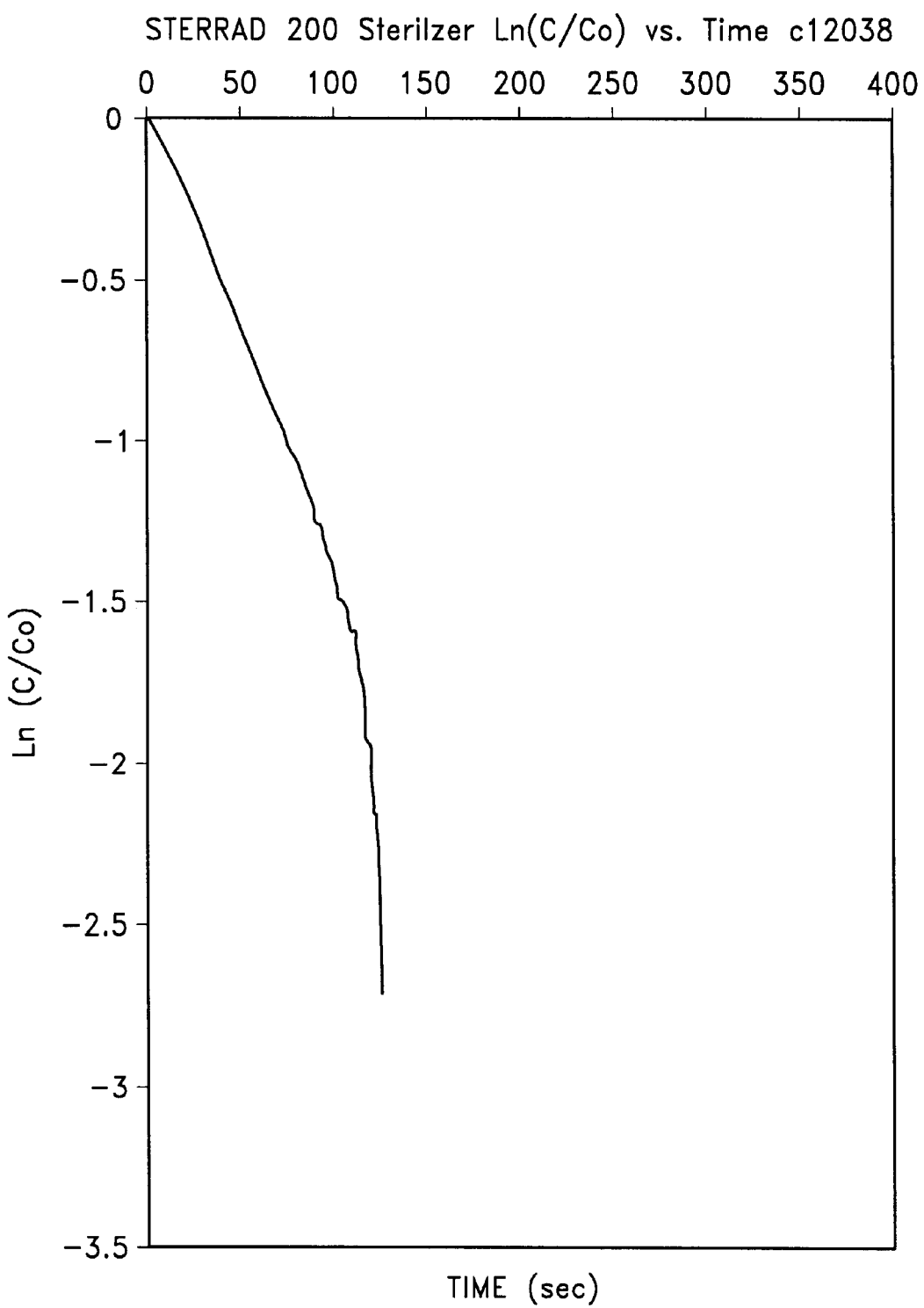
FIG. 8 is a graph of $\ln(c/c_0)$ versus time of the hydrogen peroxide concentration for a sterilization experiment with a heavy load containing a used towel.

FIGS. 5–8 show graphs of $\ln(c/c_0)$ versus time for a validation load (FIG. 5), a heavy load (FIG. 6), a heavy load with a new towel (FIG. 7), and a heavy load with an old towel (FIG. 8). The time when the concentration of hydrogen peroxide in the vacuum chamber reaches the maximum concentration is chosen to be time=0, and the maximum concentration of hydrogen peroxide is $c_0$. As best seen in FIG. 5 for the sterilization run with the validation load (run #34-1-3), the plot of $\ln(c/c_0)$ versus time is linear at short times and then deviates from linearity at longer times. It is believed that, at short times, the loss of hydrogen peroxide is due largely to the loss modes of absorption, adsorption, and condensation. After the initial rapid loss, the rate of loss of hydrogen peroxide slows, because the condensation, adsorption, and absorption sites in the chamber and on the equipment become saturated. The decrease in the concentration in hydrogen peroxide vapor at longer times is believed to be due to decomposition of the hydrogen peroxide, normally a slower process than condensation, adsorption, and absorption. In the initial part of the plot, the decomposition of hydrogen peroxide is "buried" under the faster rates of condensation, adsorption, and absorption of the hydrogen peroxide. At longer times, the rates of condensation, adsorption, and absorption are small, and the rate of decomposition of the hydrogen peroxide can be observed.

FIG. 6 shows a plot of $\ln(c/c_0)$ versus time for a run with a heavy load (run #46-6-2). The concentration of hydrogen peroxide continues to decrease rapidly for a longer time than for the validation load of FIG. 5. There is more absorption, adsorption, and/or decomposition of the hydrogen peroxide with the run with the heavy load shown in FIG. 6 than with the run with the validation load shown in FIG. 5.

FIG. 7 shows a plot of $\ln(c/c_0)$ versus time for a run with a load containing a new towel (run 91-12). Both the left hand part and the right hand part of the curve in FIG. 7 are steeper than the curves in FIGS. 5 and 6 for the validation load and heavy load, indicating more absorption, adsorption, and/or decomposition are taking place in the run shown in FIG. 7 with the load containing a new towel compared to the run with the heavy load shown in FIG. 6 or with the run with the validation load shown in FIG. 5.

FIG. 8 shows a plot of $\ln(c/c_0)$ versus time for a run with a load containing an old towel (run c12038). Please note that the y axis has a different scale than the y axis in FIGS. 5, 6, and 7. The slope of the curve for the run with the old towel is steeper than the slope for the run with the heavy load shown in FIG. 6 and the load with the new towel shown in FIG. 7, both at short and long times. The rate of absorption, adsorption, and/or decomposition of hydrogen peroxide in the run with the old towel of FIG. 8 is faster than the runs with the validation load of FIG. 5, the run with the heavy load of FIG. 6, or the run with the new towel of FIG. 7.

The curves showing the decrease in concentration of hydrogen peroxide with time shown in FIGS. 5–8 correlate with the sterilization data shown in Table 2. The sterilization of the validation loads of Group 1, as exemplified by the curve shown in FIG. 5 was more effective than the sterilization of the heavy loads of Group 2, as exemplified by the curve shown in FIG. 6. Similarly, the sterilization of the heavy loads of Group 2 was more effective than the sterilization of the heavy loads with the new towel of Group 3, as exemplified by the curve shown in FIG. 7. The Group 3 sterilizations of the heavy load with the new towel were, in turn, more effective than the sterilizations of the heavy loads with the old towel of Group 4, as exemplified by the curve shown in FIG. 8. The graphs therefore qualitatively indicate how effective the sterilization will be.

Initial Slope

At short times, the decrease in concentration of hydrogen peroxide is believed to be due to the loss modes of adsorption, absorption, and condensation. At later times, the decrease is believed to be due to decomposition of hydrogen peroxide. The initial part of the $\ln(c/c_0)$ versus time curve is therefore characteristic of the type of load. As can be seen in the graphs of $\ln(c/c_0)$ versus time in FIGS. 5–8, the curves for approximately the first 50 seconds after the peak in hydrogen peroxide concentration are nearly linear in all of the graphs. The portion of the graph for the first 50 seconds after the concentration of hydrogen peroxide vapor in the sterilization chamber reaches the maximum concentration was therefore chosen as being the portion of the curve which indicates the loss modes of absorption, absorption, and condensation.

A load containing significant quantities of materials which react with peroxide would also cause a large initial negative slope. The initial slope of the curves in the first 50 seconds after the concentration of hydrogen peroxide vapor reaches a maximum concentration in the chamber is reported as the initial slope ($-k$) in Table 2. The initial slopes in Table 2 are recorded as the negative of the initial slopes for simplicity in recording the data. It is to be understood that the initial slope is a negative number in all cases.

Although the time period of 50 seconds after the maximum concentration of hydrogen peroxide was chosen as the time period over which the initial slope was to be measured, other time periods after the maximum concentration of hydrogen peroxide concentration in the sterilization chamber may be selected as being characteristic of the initial slope of the graph of $\ln(c/c_0)$ versus time. The initial slope may be measured in the time period of less than 100 seconds after the maximum concentration of hydrogen peroxide vapor, more preferably in the time period of less than 75 seconds after the maximum concentration of hydrogen peroxide vapor, and most preferably in the time period of less than 25 seconds after the maximum concentration of hydrogen peroxide vapor. In an exemplary embodiment, the initial slope is measured in the time period of approximately 50 seconds after the maximum concentration of hydrogen peroxide vapor in the sterilization chamber.

The initial slope varies significantly with the type of load, as shown in Table 2. The initial slopes for the Group 1 runs with the validation loads range from 0.008–0.011 sec$^{-1}$ with an average of 0.00983 sec$^{-1}$. All of the BI's in the validation loads of Group 1 were negative, showing that the sterilization was effective in all cases.

The initial slopes for the Group 2 runs with the heavy loads range from 0.012–0.017 sec$^{-1}$, with an average of 0.0145 sec$^{-1}$. Only 1 of the 60 BI's in the heavy loads of Group 2 was positive, showing that the sterilization was in the quantal region.

The initial slopes for the Group 3 runs with the heavy loads and new towel ranged from 0.019–0.028 sec$^{-1}$, with an average of 0.0243 sec$^{-1}$. A total of 14/30 of the BI's in the heavy load/new towel runs of Group 3 were positive.

The initial slopes for the Group 4 runs with the heavy loads and old towel ranged from 0.025–0.039 sec$^{-1}$, with an average of 0.032 sec$^{-1}$. All 20 of the 20 BI's in the heavy load/old towel runs of Group 4 were positive.

The initial slopes for the Group 5 runs with the cold validation loads and 15 minutes of pre-plasma ranged from 0.008–0.012 sec$^{-1}$, with an average of 0.0095 sec$^{-1}$. All 72 of the BI's in the Group 5 runs were negative, showing effective sterilization.

The initial slopes for the Group 6 runs with the cold condensing validation loads with no pre-plasma ranged from 0.013–0.023 sec$^{-1}$, with an average of 0.0164 sec$^{-1}$. All of the BI's in the runs in Group 6 were negative, showing effective sterilization.

The initial slopes for the Group 7 validation loads with one towel ranged from 0.018–0.021 sec$^{-1}$, with an average of 0.0195 sec$^{-1}$. A total of 4/72 of the BI's were positive.

The initial slopes for the Group 8 validation loads with two towels ranged from 0.027–0.029 sec$^{-1}$, with an average of 0.028 sec$^{-1}$. A total of 3/73 of the BI's were positive.

The initial slope of the $\ln(c/c_0)$ versus time curve represents the reaction rate constant (−k) for loss of hydrogen peroxide from the vapor phase due to condensation, absorption, and adsorption. The initial slope changes significantly with the type of load, 0.010 sec$^{-1}$ for the validation load, 0.015 sec$^{-1}$ for the heavy load, 0.016 sec$^{-1}$ for a cold, condensing load, and >0.020 sec$^{-1}$ for the heavy load with towel. The initial rate constant can therefore be used to indicate the type of load which is present in the sterilization chamber. By knowing what type of load is present in the chamber, one can determine whether the sterilization process will be effective or not, because the type of load has been shown to correlate with the effectiveness of the sterilization.

Because the initial slope of the $\ln(c/c_0)$ versus time curve can be determined rapidly after reaching the peak concentration of hydrogen peroxide, for example 50 seconds in the results in Table 2, the compatibility of the load with the sterilization process can be determined rapidly and conveniently after the start of the sterilization process. If the load is incompatible with the sterilization process due to absorption, adsorption, condensation, or decomposition of hydrogen peroxide, the run can be terminated quickly, allowing another cycle to be started after the incompatible materials are removed from the load.

The acceptable slope from the empirically determined data generally is chosen to achieve a reduction in the microorganisms of at least 6 log or a reduction to less than or equal to 10−6 of the initial level. Based on the initial slopes and the sterilization data shown in Table 2, the run should be aborted if the negative of the initial slope of a graph of $\ln(c/c_0)$ versus time is 0.016 sec$^{-1}$ or less, more preferably 0.014 sec$^{-1}$ or less, and most preferably 0.013 sec$^{-1}$ or less, where the initial slope is the slope in approximately the first 50 seconds after the concentration of hydrogen peroxide reaches its peak concentration.

A similar series of experiments can be carried out with other germicide vapors or germicide gases to empirically determine limits for the initial slopes for graphs of $\ln(c/c_0)$ versus time for other germicide gases. Suitable vaporizable germicides for the method include, but are not limited to, peracetic acid and formaldehyde. Suitable germicide gases include, but are not limited to ethylene dioxide and chlorine dioxide.

Final Hydrogen Peroxide Concentration

The final concentration of hydrogen peroxide is another good indicator of the suitability of the load. The final concentration is measured at the end of the diffusion step 50, prior to evacuating and generating the post-injection plasma. The final concentration $C_f$ of hydrogen peroxide in the Group 1 validation load runs in Table 2 was 0.86–1.02 mg/L, and all of the BI's for the validation runs were negative for growth.

With the Group 2 heavy load runs, the final concentration of hydrogen peroxide was 0.46–0.51 mg/L. The BI's for the Group 2 heavy load runs were bordering on the quantal region.

The final concentrations of hydrogen peroxide for the Group 3 and Group 4 runs with heavy loads and towels ranged from 0–0.24 mg/L, and there were many positive BI's.

If the load is not suitable for sterilization, the load will absorb, adsorb, condense, or decompose hydrogen peroxide, reducing the concentration of hydrogen peroxide in the chamber. Because the hydrogen peroxide concentration has been reduced, the final concentration will be reduced, and the sterilization will not be as effective.

The final concentration of hydrogen peroxide in the sterilization chamber can therefore be used as an alternative indication of the suitability of the load for sterilization. If the final concentration of hydrogen peroxide in the sterilization chamber is 0.47 mg/L or greater, more preferably 0.86 or greater, and most preferably 0.90 or greater, the operator can be assured that the sterilization will be effective. The limits on the final concentration of hydrogen peroxide depend on the cycle conditions. Lower concentrations may be effective, depending on the cycle time or temperature.

The disadvantage of using the final concentration of hydrogen peroxide for determining the suitability of the load is that the final concentration of hydrogen peroxide cannot be determined until the diffusion phase is over, about 1–45 minutes after the hydrogen peroxide has been injected.

In contrast, the slope of the $\ln(c/c_0)$ versus time line can be determined about a minute after the peak concentration of hydrogen peroxide. If the slope of the $\ln(c/c_0)$ versus time line is consistent with the load being unsuitable for sterilization, the run can be aborted and a new cycle started, saving a great deal of time, increasing the efficiency of both the equipment and the operating personnel. Further, by aborting the run quickly, the equipment will have less time to absorb, adsorb, or condense hydrogen peroxide or vaporizable germicide, minimizing the time required to remove the hydrogen peroxide from the equipment.

The final concentration index is perhaps most useful in clearly distinguishing between the Group 1 validation loads and the Group 2 heavy loads. The average final concentration of hydrogen peroxide for the Group 1 validation loads was 0.92 mg/L compared to an average concentration of 0.48 mg/L for the Group 2 heavy loads. The final concentration index therefore clearly distinguishes between the Group 1 validation loads and the Group 2 heavy loads.

It is apparent that sterilization of the load cannot be achieved if there is not enough hydrogen peroxide in the chamber. The determination of the peroxide concentration in the chamber therefore does not need to wait until the end of step 46. As soon as the peroxide concentration decreases below the acceptable level, the cycle can be canceled or aborted. The end of the injection stage 46 can therefore be determined by having an acceptable concentration of hydrogen peroxide vapor in the chamber for the length of time which was planned for the injection stage 46. In this case, the sterilization cycle would be considered an acceptable cycle, and the remaining steps of the normal cycle would be performed.

Alternatively, the end of the injection stage 46 can be determined by having the concentration of vapor phase hydrogen peroxide drop below an acceptable concentration. In that case, the cycle would be considered unacceptable, and the cycle could be aborted and a new sterilization cycle.

Area Under the Curve

The area under the curve of a plot of concentration versus time in Table 2 represents the variation in the concentration during the injection step in a single index which changes with the type of load. The area may be calculated either from the beginning of injection or from the time of maximum hydrogen peroxide concentration. The areas in Table 2 were measured from the time of maximum hydrogen peroxide concentration.

The average area under the curve for the Group 1 validation runs was 512 mg-sec/L, compared to 399 mg-sec/L for the Group 2 heavy loads. The average area under the curve decreased to 177 mg-sec/L for the Group 3 heavy loads with a new towel and to 97 mg-sec/L for the Group 4 heavy loads with old towels. The area under the curve is preferably greater than 400 mg-sec/L, more preferably greater than 450 mg-sec/L, and most preferably greater than 500 mg-sec/L.

The area under the curve can therefore be used as an alternative indication of the suitability of the load. The area under the curve cannot be determined until the end of the injection period, however, far later in the sterilization run than for the initial slope method. The area under the curve method is largely useful for being able to better distinguish between the Group 1 validation loads and the Group 2 heavy loads than for most of the rest of the methods. The only method more useful for distinguishing the Group 1 from the Group 2 loads is the final concentration of hydrogen peroxide.

Determination of the initial slope of the plot of the $\ln(c/c_0)$ versus time therefore provides a convenient, rapid method of determining the suitability of a load of equipment for sterilization. If the equipment in the load absorbs, adsorbs, condenses, or decomposes significant amounts of hydrogen peroxide, the initial slope of the curve will be steeper than if the equipment in the load is suitable for sterilization. If the equipment is unsuitable, the sterilization run can be terminated, saving operator time and minimizing the amount of hydrogen peroxide which is absorbed, adsorbed, or condensed by the equipment.

If the method of initial slope is used to determine the suitability of the load for sterilization with other vaporizable germicides, the ranges of the initial slope which lead to acceptable sterilization are determined experimentally.

The suitability of the load can also be determined with the final hydrogen peroxide concentration or the area under the curve. For an acceptable load, the injection time for step 46 is the pre-determined injection time to ensure the sterility of the load. For an unacceptable load, the injection time for step 46 is the time when process control 30 detects either a nonacceptable concentration or a nonacceptable area. For an unacceptable load, the cycle can be aborted immediately to minimize the absorption, adsorption, or condensation of hydrogen peroxide on the load.

Figure 9:
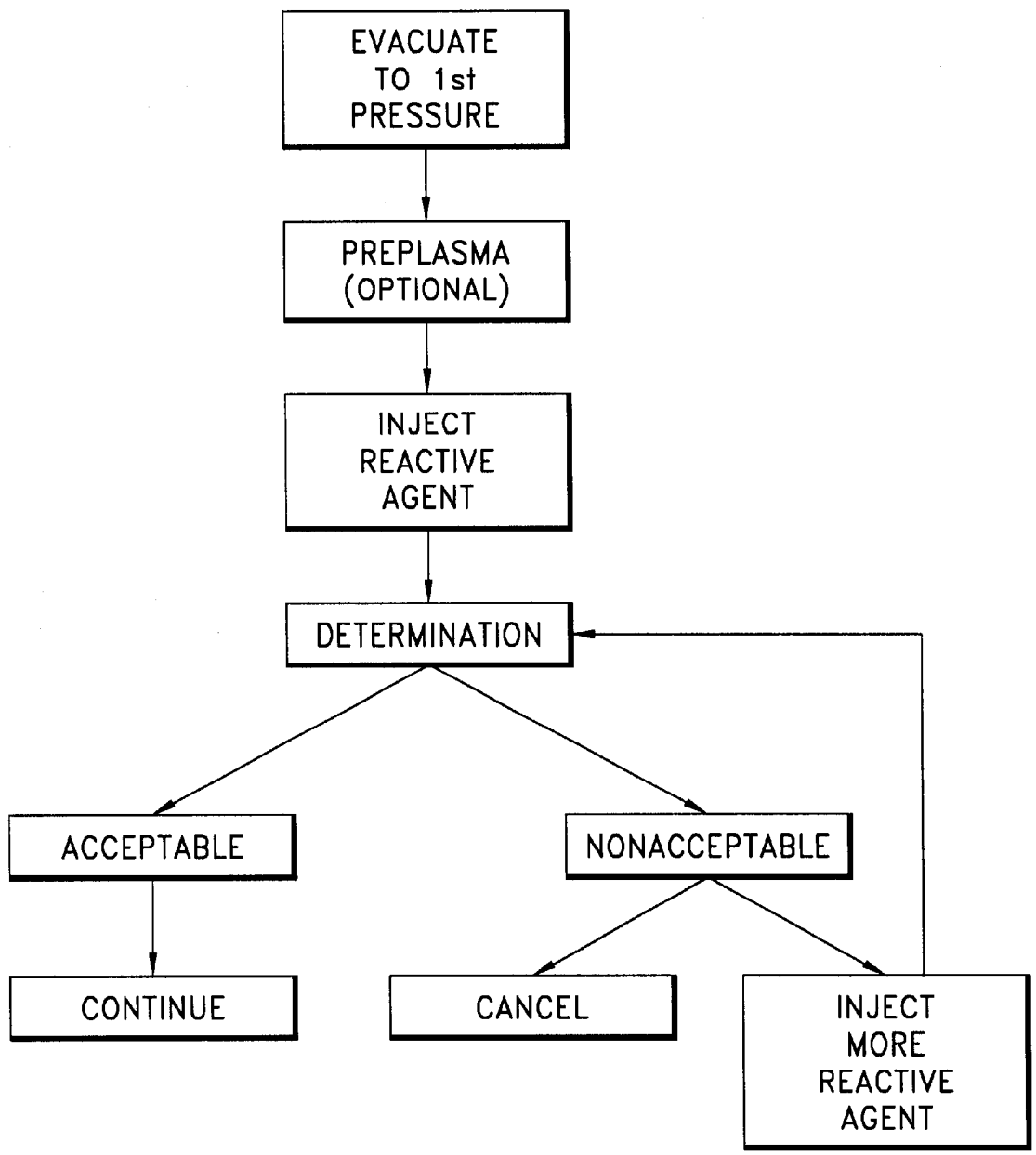
FIG. 9 is a diagram of a decision tree showing the alternatives when the acceptability of the load for sterilization with a reactive agent has been determined.

FIG. 9 shows a decision tree for the determination of suitability of a load for sterilization with a vaporizable germicide or germicide gas. In the embodiments of the method of the invention, the chamber is evacuated to a first pressure. Plasma can optionally be introduced into the chamber to dry the equipment to be sterilized. The reactive agent is then injected into the chamber. Although it is generally preferred to introduce plasma into the chamber prior to injection of the reactive agent, introduction of plasma is optional.

After the injection of the reactive agent, the suitability of the load is determined. The suitability of the load may be determined in any suitable manner including, but not limited to, the initial slope of a graph of $\ln(c/c_0)$ versus time, the initial slope of a graph of $\log_{10}(c/c_0)$ versus time, the area under the curve of a graph of $\ln(c/c_0)$ versus time, the area under the curve of a graph of $\log_{10}(c/c_0)$ versus time, or by the final concentration of the reactive agent.

If the load is suitable or acceptable, the cycle is continued. If the load is not suitable or not acceptable, the cycle can be canceled. Alternatively, more reactive agent can be injected to try to overcome the nonacceptablity of the load. In an exemplary embodiment, more reactive agent is injected one more time. If the load is still nonacceptable after reactive agent has been injected a second time, the cycle is preferably canceled.

Although the method has been described with hydrogen peroxide as an example, the method may also be applied to any vaporizable germicide or germicide gas. The acceptable slope of the graph of $\ln c/c_0$ versus time for each vaporizable germicide or germicide gas can be determined by performing a series of experiments with a variety of types of loads, as described herein for the example of hydrogen peroxide.

If the embodiments of the method are applied to a vaporizable germicide, the vaporizable germicide can be absorbed, adsorbed, decomposed, or condensed, by the equipment in the load. If the embodiments of the method are applied to a germicide gas, the germicide gas can be absorbed, adsorbed, or decomposed by the equipment.

Some examples of vaporizable germicide which are suitable for embodiments of the method of the present invention include, but are not limited to, peracetic acid and formaldehyde. Some examples of germicide gas which are suitable for embodiments of the method of the present invention include, but are not limited to, ethylene dioxide and chlorine dioxide.

Various modifications and alterations of this invention will be apparent to those skilled in the art without departing from the scope and spirit of this invention. It should be understood that the invention is not limited by the embodiments disclosed therein and that the claims should be interpreted as broadly as the prior art allows.

What is claimed is:

1. A method for sterilizing a load with a germicide vapor or gas comprising:

placing the load into a sterilization chamber;

evacuating the sterilization chamber;

contacting the load in the sterilization chamber with the germicide vapor or gas;

monitoring a concentration of said germicide vapor or gas in the sterilization chamber as a function of time;

determining a rate of change of the concentration of said germicide vapor or gas in said sterilization chamber;

determining the suitability of the load from said rate of change; and sterilizing the load, wherein the load is suitable for sterilization if the rate of change is less than an empirically-derived rate at which a predetermined level of sterilization is achieved.

2. The method of claim 1, wherein said pre-determined level of sterilization is a reduction in microorganisms to a level of $10^{-6}$ or less of an initial level.

3. The method of claim 1, wherein the suitability of the load is determined less than 100 seconds after contacting the load with the germicide vapor or gas.

4. The method of claim 1, wherein the rate of change of the concentration is determined as the initial slope of a graph of $\log_x(c/c_0)$ versus time, where x is any number, c is the concentration of said germicide gas or vapor, and $c_0$ is a maximum concentration of said germicide gas or vapor in said sterilization chamber.

5. The method of claim 4, wherein $\log_x$ is selected from the group consisting of $\log_{10}$ and ln.

6. The method of claim 4, wherein said germicide gas or vapor comprises hydrogen peroxide vapor.

7. The method of claim 6, further comprising contacting said load with plasma before contacting said load with hydrogen peroxide vapor.

8. The method of claim 6, further comprising determining said load is unsuitable if the negative of said initial slope is 0.016 sec$^{-1}$ or greater, where $\log_x$ is ln.

9. The method of claim 1, further comprising aborting the sterilization if the load is determined to not be suitable.

10. The method of claim 9, wherein said aborting comprises evacuating said sterilization chamber after said determining or generating plasma in said sterilization chamber after said determining.

11. The method of claim 8, further comprising adding more hydrogen peroxide into said sterilization chamber.

12. The method of claim 6, wherein said monitoring comprises measuring a concentration of hydrogen peroxide vapor with a spectrometer or measuring an quantity of heat evolved by a reaction of said hydrogen peroxide vapor with a chemical compound.

13. The method of claim 1, further comprising adding germicide gas or vapor if the load is determined to be not suitable.

14. A method for sterilizing a load with a germicide vapor or gas comprising:

placing the load into a sterilization chamber;

evacuating the sterilization chamber;

contacting the load in the sterilization chamber with germicide vapor or gas;

monitoring a concentration of said germicide vapor or gas in the sterilization chamber as a function of time;

determining an area under a curve of a graph of c versus time, where c is the concentration of said germicide vapor or gas;

determining the suitability of the load from said area; and sterilizing the load, wherein the load is suitable for sterilization if the area is greater than an empirically derived area with which a predetermined level of sterilization is achieved.

15. The method of claim 14, wherein said germicide vapor or gas comprises hydrogen peroxide.

16. The method of claim 14, wherein the area under the curve is determined from a time of the maximum concentration of said germicide vapor or gas to a time at an end of said contacting with germicide vapor or gas and wherein the load is suitable if the area under the curve is greater than 400 mg-sec/L.

17. The method of claim 14, further comprising aborting the sterilization if the load is determined to be not suitable.

18. The method of claim 14, further comprising adding germicide gas or vapor if the load is determined to be not suitable.

19. A method for sterilizing a load with a germicide vapor or gas comprising:

placing the load into a sterilization chamber;

evacuating the sterilization chamber;

contacting the load in the sterilization chamber with germicide vapor or gas;

determining a concentration of said germicide vapor or gas; and determining the suitability of the load from said concentration; and sterilizing the load, wherein the load is suitable for sterilization if the concentration is greater than an empirically derived concentration with which a pre-determined level of sterilization is achieved.

20. The method of claim 19, further comprising aborting the sterilization if the load is determined to be not suitable.

21. The method of claim 19, wherein said germicide vapor or gas comprises hydrogen peroxide.

22. The method of claim 21, wherein the load is suitable for sterilization if the concentration of germicide vapor or gas is 0.47 mg/L or greater.

23. The method of claim 19, further comprising adding germicide gas or vapor if the load is determined to be not suitable.

* * * * *